(12) United States Patent
Johnson

(10) Patent No.: US 9,827,176 B2
(45) Date of Patent: Nov. 28, 2017

(54) ANTIFUNGAL DEODORANT

(71) Applicant: Shirley Johnson, Memphis, TN (US)

(72) Inventor: Shirley Johnson, Memphis, TN (US)

( * ) Notice: Subject to any disclaimer, the term of this patent is extended or adjusted under 35 U.S.C. 154(b) by 107 days.

(21) Appl. No.: 14/813,226

(22) Filed: Jul. 30, 2015

(65) Prior Publication Data

US 2016/0136067 A1     May 19, 2016

Related U.S. Application Data

(60) Provisional application No. 62/080,963, filed on Nov. 17, 2014.

(51) Int. Cl.
| | |
|---|---|
| *A61K 8/26* | (2006.01) |
| *A61Q 15/00* | (2006.01) |
| *A61K 31/085* | (2006.01) |
| *A61K 31/341* | (2006.01) |
| *A61K 31/045* | (2006.01) |
| *A61K 31/704* | (2006.01) |
| *A61K 31/01* | (2006.01) |
| *A61K 31/00* | (2006.01) |

(52) U.S. Cl.
CPC ............... *A61K 8/26* (2013.01); *A61K 31/00* (2013.01); *A61K 31/01* (2013.01); *A61K 31/045* (2013.01); *A61K 31/085* (2013.01); *A61K 31/341* (2013.01); *A61K 31/704* (2013.01); *A61Q 15/00* (2013.01)

(58) Field of Classification Search
None
See application file for complete search history.

(56) References Cited

U.S. PATENT DOCUMENTS

| | | | | |
|---|---|---|---|---|
| 5,641,475 | A | * | 6/1997 | Yu .......................... A23L 3/3481 252/397 |
| 5,807,890 | A | | 9/1998 | Yu et al. |
| 5,874,071 | A | | 2/1999 | Yu et al. |
| 5,958,975 | A | | 9/1999 | Yu et al. |
| 6,548,052 | B2 | | 4/2003 | Rosenberg |
| 2001/0041169 | A1 | * | 11/2001 | Allan ..................... A45D 40/16 424/65 |
| 2006/0104940 | A1 | * | 5/2006 | Heinrichs ............ A61K 8/8152 424/78.03 |
| 2007/0141013 | A1 | * | 6/2007 | Nguyen-Kim ....... A61K 8/8158 424/70.15 |

\* cited by examiner

*Primary Examiner* — Robert A Wax
*Assistant Examiner* — Quanglong Truong
(74) *Attorney, Agent, or Firm* — David J. Kreher

(57) ABSTRACT

A prophylactic cream, ointment or deodorant for the prevention of the formation of yeast infections.

6 Claims, No Drawings

ANTIFUNGAL DEODORANT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

DESCRIPTION

Field of the Invention

The present disclosure reveals an antifungal deodorant for the purpose of preventing yeast infections and a method of making the same.

BACKGROUND OF THE INVENTION

A yeast infection of the skin is a fungal infection caused by yeast-like fungi called *candida* that causes a red, scaling, itchy rash on the skin. This fungi breakout may affect nearly any skin surface on the body, but are most likely to occur in warm, moist, creased areas including the armpits, groin, and breast region. Yeast inflections are especially common among people who are obese or who have diabetes and are commonly treated with medicated creams. To date, there are no prophylactic ointments, creams, lotions, or solids available to prevent yeast infections. For example, the primary function of deodorants is to prevent odor. This is usually accomplished in three ways: First, the suppression of perspiration; second, the use of antibacterial agents to prevent the growth of bacteria that produce the undesirable odor; or third, by masking the odor with perfumes. However, deodorants are not designed to address yeast infections.

The present disclosure reveals an antifungal deodorant that can be applied to the skin that prevents the development of the fungi that produce yeast infections. Several deodorants have been developed to prevent the growth of odor producing bacteria but none prevent the development of the fungi that produce yeast infections.

AMENDED SUMMARY OF THE INVENTION

A prophylactic cream, ointment or deodorant for yeast infections comprising at least one anti-microbial agent, at least one anti-chaffing agent, at least one vasoconstrictor, at least one antiperspirant, and Isododecane. The at least one anti-microbial agent comprisinga mixture of Phenoxyethanol and Sorbitancaprylate. The at least one anti-chaffing agent comprises alpha bisabolol. The at least one vasoconstrictor comprises Escin. The at least one antiperspirant comprises aluminum chlorohydrate.

The first embodiment of the prophylactic comprises:

| Material | Weight Percent |
| --- | --- |
| Cetearyl alcohol 30/70 NF | 20.00-40.00% |
| Trioctonoin | 1.00-2.00% |
| Glyceryl Stearate | 1.00-3.00% |
| Cyclomethicone | 25.00-35.00% |
| Coconut oil | 2.00-6.00% |
| Isododecane | 6.00-8.00% |
| Aerosil R 972 | 5.00-9.00% |
| Aluminum chlorohydrate | 5.00-15.00% |
| Alpha bisabolol | 0.05-0.15% |
| Escin | 0.005-0.015% |
| Phenoxyethanol and Sorbitancaprylate | 1.00-3.00% |
| Propylene glycol | 3.50-4.50% |

The second embodiment of the prophylactic treatment comprises:

| Material | Weight Percent |
| --- | --- |
| Cetearyl alcohol 30/70 NF | 10.00-20.00% |
| Cetyl esters NF | 10.00-20.00% |
| Trioctonoin | 1.00-2.00% |
| Glyceryl Stearate | 1.00-3.00% |
| Cyclomethicone | 25.00-35.00% |
| Coconut oil | 2.00-6.00% |
| Isododecane | 6.00-8.00% |
| Aerosil R 972 | 5.00-9.00% |
| Aluminum chlorohydrate | 5.00-15.00% |
| Alpha bisabolol | 0.05-0.15% |
| Escin | 0.005-0.015% |
| Phenoxyethano and Sorbitancaprylate) | 1.00-3.00% |
| Propylene glycol | 3.50-4.50% |

BRIEF DESCRIPTION OF THE SEVERAL VIEWS OF THE DRAWING

Not Applicable

AMENDED DETAILED DESCRIPTION OF THE INVENTION

The present disclosure reveals a prophylactic cream, ointment or deodorant for yeast infections comprising at least one anti-microbial agent, at least one anti-chaffing agent, at least one vasoconstrictor, at least one antiperspirant, and Isododecane.

Said anti-microbial agent is selected from the group consisting of a mixture of Phenoxyethanol and Sorbitancaprylate, parabens, alcohol, benzoic acid, boraxitrus seed extracts, copper salts, fragrance oils, glycerin, hinokitiol, honey, japanese honeysuckle extracts, melaleucol (tea tree) oil, perillic acid, salicylic acid, Salt, silver chloride, sodium gluconate, sorbic acid, sugar, usnic acid, wasabi extract, zinc salts, citrus grandis, Germaben II, Germaben II-E, phenoxyethanol, potassium sorbate, benzylalcohol, tetrasodium EDTA, phenoxyethanol, and Germall Plus.

Said anti-chaffing agent is selected form a group consisting of aloe vera gel, alpha bisabolol, allantoin, sorbitol, urea, lactic acid and salts, glucose derivatives, zinc acetate, zinc carbonate, zinc oxide, potassium gluconate, dimethicone, glycerin, petrolatum, lanolin, peramides, uric acid and salts, N-acetyl cysteine, and hydrocortisone.

Said vasoconstrictor is selected from a group consisting of horse chestnut extract (*aesculus hippocastanum* extract)), Esculin, Escin, Yohimbine, *Capsicum* Oleoresin, Capsaicin, niacin, niacin Esters, methyl nicotinate, benzyl nicotinate, ruscogenins (butchers broom extract; *ruscus aculeatus* extract), diosgenin (*trigonella foenumgraecum*, fenugreek), emblica extract (phyllanthus emblica extract), asiaticoside (*centella asiatica* extract), boswellia Extract (*boswellia serrata*), ginger root extract (*zingiber officianalis*), piperine, vitamin K, melilot (*melilotus officinalis* extract), glycyrrhetinic acid, ursolic acid, sericoside (*terminalia sericea* extract), darutoside (*siegesbeckia orientalis* extract), amni visnaga extract, extract of red vine (*vitis vinifera*) leaves, apigenin, phytosan, and luteolin.

Said antiperspirant is selected from the group comprising of the aluminum chlorohydrates, the aluminum chlorohydrates, aluminum chloride, and aluminum zirconium tetrachlorohydrex gly.

Said prophylactic treatment wherein the at least one anti-microbial agent comprises a mixture of Phenoxyethanol and Sorbitancaprylate, the at least one anti-chaffing agent comprises alpha bisabolol, the at least one vasoconstrictor comprises Escin, the at least one antiperspirant comprises aluminum chlorohydrate, and Isododecane.

The first embodiment of the prophylactic cream, ointment or deodorant comprises;
 a. Bisabolol 0.05-0.15%;
 b. Phenoxyethanol and Sorbitancaprylate 1.00-3.00%;
 c. Escin 0.005-0.015%;
 d. Aluminum chlorohydrate 5.00-15.00%; and
 e. Isododecane 6.00-8.00%.

The first embodiment of the prophylactic cream, ointment or deodorant further comprises:
 a. Cetearyl alcohol 30/70 NF; 20.00-40.00%;
 b. Trioctonoin 1.00-2.00%;
 c. Glyceryl stearate 1.00-3.00%;
 d. Cyclomethicone 25.00-35.00%
 e. Coconut oil 2.00-6.00%;
 f. Aerosol R 972 5.00-15.00%; and
 g. Propylene glycol 3.50-4.50%.

The first embodiment of the prophylactic cream, ointment or deodorant wherein the method of compilation comprises first combining cetearyl alcohol 30/70 NF, trioctonoin, glyceryl stearatge, cyclomethicone, and coconut oil. Next, these ingredients are heated to 75° C. to melt and stir the mixture under low to medium speeds. Once these ingredients have been melted and mixed, the temperature is maintained 75° C. Continue by adding Aerosol R 972, aluminim chlorohydrate, alpha bisabolol, and Escin, while continuing to maintain the mixtures temperature at 75° C. Continue to mix at low to medium speeds. Once the Aerosol R 972 specifically looks to be incorporated increase mixing speeds to medium to high for at least 5 minutes to ensure the Aerosol R 972 is properly incorporated into the mixture. Next, adda mixture of Phenoxyethanol and Sorbitancaprylate, propylene glycol and any fragrance at low to medium mixing speeds. At this point the heat can kept at 60° C. Allow for another 5 minutes of mixing. Once all the ingredients have been sufficiently mixed together pour the contents into an empty "stick" deodorant applicator and allow ample time for the mixture to solidify before any application or evaluation. This mixture should be kept heated at 60-75° C. while filling to avoid crystallization of product.

The second embodiment of the prophylactic cream, ointment tor deodorant again comprises the original concentrations as follows:
 a. Bisabolol 0.05-0.15%;
 b. Phenoxyethanol and Sorbitancaprylate 1.00-3.00%;
 c. Escin 0.005-0.015%;
 d. Aluminum chlorohydrate 5.00-15.00%; and
 e. Isododecane 6.00-8.00%.

The second embodiment of the prophylactic cream, ointment or deodorant further comprises:
 a. Cetearyl alcohol 3-/70 NF 10.00-20.00%;
 b. Cetyl esters NF 10.00-20.00%;
 c. Trioctonoin 1.00-2.00%;
 d. Glyceryl stearate 1.00-3.00%;
 e. cyclomethicone 25.00-35.00%;
 f. coconut oil 2.00-6.00%;
 g. aerosol R 972 5.00-9.00%
 h. propylene glycol 3.50-4.50%

The second embodiment of the prophylactic treatment wherein the method of compilation comprises first combining cetearyl alcohol 30/70 NF, cetyl esters NF, trioctonoin, glyceryl stearate, cyclomethicone and coconut oil. Next, heating these ingredients to 75° C. to melt and stir the mixture under low to medium speeds. Once these ingredients have been melted and mixed, maintain its temperature at 75° C. Next, add isododecane while still maintaining the mixtures temperature at 75° C. and mixing under low to medium speeds. Now add Aerosol R 972, aluminum chlorohydrate, alpha bisabolol and Escin, while continuing to maintain the mixtures temperature at 75° C. Initially continue to mix at low to medium speeds. Once the Aerosol R 972 specifically looks to be incorporated increase mixing speeds to medium to high for at least 5 minutes to ensure the Aerosol R 972 is properly incorporated into the mixture. Next, add a mixture of Phenoxyethanol and Sorbitancaprylate, propylene glycol and any fragrance at low to medium mixing speeds. At this point the heat can kept at 60° C. Allow for another 5 minutes of mixing. Once all the ingredients have been sufficiently mixed together pour the contents into an empty "stick" deodorant applicator and allow ample time for the mixture to solidify before any application or evaluation. This mixture should be kept heated at 60-75° C. while filling to avoid crystallization of product.

What is claimed:

1. A prophylactic cream, ointment or deodorant for yeast infections comprising:
 at least one anti-microbial agent, at least one anti-chafing agent, at least one vasoconstrictor, at least one antiperspirant, and isododecane;
 wherein the at least one anti-microbial agent comprises phenoxyethanol and sorbitan caprylate);
 the at least one anti-chafing agent comprises alpha bisabolol;
 the at least one vasoconstrictor comprises escin; and
 the at least one antiperspirant comprises aluminum chlorohydrate.

2. The prophylactic cream, ointment or deodorant of claim 1 comprising;
 a. bisabolol 0.05-0.15% by weight;
 b. phenoxyethanol and sorbitan caprylate 1.00-3.00% by weight;
 c. escin 0.005-0.015% by weight;
 d. aluminum chlorohydrate 5.00-15.00% by weight; and
 e. isododecane 6.00-8.00% by weight
 f. fragrance 1.00-5.00% by weight.

3. The prophylactic cream, ointment or deodorant of claim 2 further comprising;
 a. cetearyl alcohol 20.00-40.00% by weight;
 b. trioctonoin 1.00-2.00% by weight;
 c. glyceryl stearate 1.00-3.00% by weight;
 d. cyclomethicone 25.00-35.00% by weight
 e. coconut oil 2.00-6.00% by weight;
 f. fumed silica 5.00-15.00% by weight;
 g. propylene glycol 3.50-4.50% by weight; and
 h. fragrance 1.00-5.00% by weight.

4. A method of making a prophylactic cream, ointment or deodorant as claimed in claim 3 wherein the method of making comprises;
   a. combining cetearyl alcohol, trioctanoin, glyceryl stearate, cyclomethicone, and coconut oil;
   b. these ingredients are then heated to 75° C. to melt and stir the mixture under low to medium speeds;
   c. once these ingredients have been melted and mixed, the temperature of the mixture is maintained at 75° C.;
   d. next add to the mixture fumed silica, aluminim chlorohydrate, alpha bisabolol, and escin, while continuing to maintain the mixture's temperature at 75° C.;
   e. initially continue to mix the mixture at low to medium speeds;
   f. once the fumed silica specifically looks to be incorporated increase mixing speeds to medium to high for at least 5 minutes to ensure the fumed silica is properly incorporated into the mixture;
   g. next add a mixture of phenoxyethanol and sorbitan caprylate, propylene glycol and any fragrance at low to medium mixing speeds;
   h. at this point the heat can be kept at 60° C.;
   i. allow for another 5 minutes of mixing;
   j. once all the ingredients have been sufficiently mixed together pour the mixture into an empty "stick" deodorant applicator and allow ample time for the mixture to solidify before any application or evaluation; and
   k. this mixture should be kept heated at 60-75° C. while filling to avoid crystallization of product.

5. The prophylactic cream, ointment or deodorant of claim 2 wherein the amounts of listed ingredients are further specified as follows:
   a. cetearyl alcohol 10.00-20.00% by weight;
   b. cetyl esters 10.00-20.00% by weight;
   c. trioctonoin 1.00-2.00% by weight;
   d. glyceryl stearate 1.00-3.00% by weight;
   e. cyclomethicone 25.00-35.00% by weight;
   f. coconut oil 2.00-6.00% by weight;
   g. fumed silica 5.00-9.00% by weight
   h. propylene glycol 3.50-4.50% by weight
   i. fragrance 1.00-5.00% by weight.

6. A method of making a prophylactic cream, ointment or deodorant as claimed in claim 5 wherein the method of making comprises:
   a. combining cetearyl alcohol, cetyl esters, trioctanoin, glyceryl stearate, cyclomethicone and coconut oil;
   b. next heat the mixture of these ingredients to 75° C. to melt and stir the mixture under low to medium speeds;
   c. once these ingredients have been melted and mixed, maintain its temperature at 75° C.;
   d. next, into the mixture, add isododecane while still maintaining the mixtures temperature at 75° C. and mixing under low to medium speeds;
   e. also add fumed silica, aluminum chlorohydrate, alpha bisabolol and escin, while continuing to maintain the mixtures temperature at 75° C.;
   f. initially continue to mix the mixture at low to medium speeds;
   g. once the fumed silica specifically looks to be incorporated, increase mixing speeds to medium to high for at least 5 minutes to ensure the fumed silica is properly incorporated into the mixture;
   h. next add a mixture of phenoxyethanol and sorbitan caprylate, propylene glycol and any fragrance at low to medium mixing speeds;
   i. at this point the heat can be kept at 60° C.;
   j. allow for another 5 minutes of mixing;
   k. once all the ingredients have been sufficiently mixed together pour the contents of the mixture into an empty "stick" deodorant applicator and allow ample time for the mixture to solidify before any application or evaluation; and
   l. this mixture should be kept heated at 60-75° C. while filling to avoid crystallization of product.

* * * * *